US012637654B2

(12) United States Patent
Bode et al.

(10) Patent No.: US 12,637,654 B2
(45) Date of Patent: May 26, 2026

(54) BIOPROCESSING INSTALLATION

(71) Applicant: Sartorius Stedim Biotech GmbH, Goettingen (DE)

(72) Inventors: Matthias Bode, Bodensee (DE); Swen Weitemeier, Loedingsen (DE); Alexander Zilaev, Bovenden (DE); Manuel Juenemann, Katlenburg-Lindau (DE); Anne-Lise Damiano, Carnoux-en-Provence (FR); Bernhard Diel, Dransfeld (DE)

(73) Assignee: Sartorius Stedim Biotech Gmbh, Goettingen (DE)

( * ) Notice: Subject to any disclaimer, the term of this patent is extended or adjusted under 35 U.S.C. 154(b) by 898 days.

(21) Appl. No.: 17/800,469

(22) PCT Filed: Nov. 27, 2020

(86) PCT No.: PCT/EP2020/083698
§ 371 (c)(1),
(2) Date: Aug. 17, 2022

(87) PCT Pub. No.: WO2021/164912
PCT Pub. Date: Aug. 26, 2021

(65) Prior Publication Data
US 2023/0077918 A1     Mar. 16, 2023

(30) Foreign Application Priority Data
Feb. 18, 2020    (EP) ..................................... 20315021

(51) Int. Cl.
*C12M 1/36*      (2006.01)
*B65B 3/00*      (2006.01)
(Continued)

(52) U.S. Cl.
CPC ............. *C12M 41/48* (2013.01); *B65B 3/003* (2013.01); *B65B 57/10* (2013.01); *C12M 23/40* (2013.01);
(Continued)

(58) Field of Classification Search
CPC ............ A61J 1/05; A61J 1/10; A61J 2200/70; B65B 3/003; B65B 57/10; C12M 23/40;
(Continued)

(56) References Cited

FOREIGN PATENT DOCUMENTS

DE     102011000430      8/2012
JP       2009539606 A   *   11/2009   ............. B65D 83/00
(Continued)

OTHER PUBLICATIONS

"Extended European Search Report," for European Patent Application No. 20315021.4 mailed Sep. 9, 2020 (7 pages).
(Continued)

*Primary Examiner* — Michael L Hobbs
(74) *Attorney, Agent, or Firm* — Pauly, DeVries Smith & Deffner LLC

(57) ABSTRACT

A bioprocessing installation comprising a reservoir tank, one or more fluid lines, one or more receiving containers and an electronic control unit. The fluid line fluidically connects the reservoir tank to a receiving container. The liquid biological medium can be transferred from the reservoir tank through the fluid line into the at least one receiving container. The bioprocessing installation comprises a sensor arrangement with at least one gas bubble sensor, which sensor arrangement is configured to detect one or more gas bubbles or foam or separated phases in the liquid biological medium by a gas bubble sensor and to generate one or more corresponding sensor signals, and the electronic control unit is configured to monitor the transfer of the liquid biological medium from
(Continued)

the reservoir tank in the direction of the at least one receiving container based on the sensor signals generated by the sensor arrangement.

21 Claims, 1 Drawing Sheet

(51) Int. Cl.
    *B65B 57/10*        (2006.01)
    *C12M 1/00*        (2006.01)
    *C12M 1/34*        (2006.01)

(52) U.S. Cl.
    CPC ............ *C12M 29/04* (2013.01); *C12M 41/34*
             (2013.01); *C12M 41/44* (2013.01)

(58) Field of Classification Search
    CPC ...... C12M 29/04; C12M 41/34; C12M 41/44;
                             C12M 41/48
    See application file for complete search history.

(56) References Cited

FOREIGN PATENT DOCUMENTS

| WO | 2017141206 | | 8/2017 | |
| WO | WO-2017141206 | A1 * | 8/2017 | ............ G01G 17/06 |
| WO | 2017158009 | | 9/2017 | |
| WO | 2019155032 | | 8/2019 | |
| WO | WO-2019155032 | A1 * | 8/2019 | ........... C12M 29/10 |
| WO | 2021164912 | | 8/2021 | |

OTHER PUBLICATIONS

"International Search Report and Written Opinion," for PCT Application No. PCT/EP2020/083698 mailed Feb. 18, 2021 (15 pages).
"International Preliminary Report on Patentability," for PCT Application No. PCT/EP2020/083698 mailed Sep. 1, 2022 (9 pages).

* cited by examiner

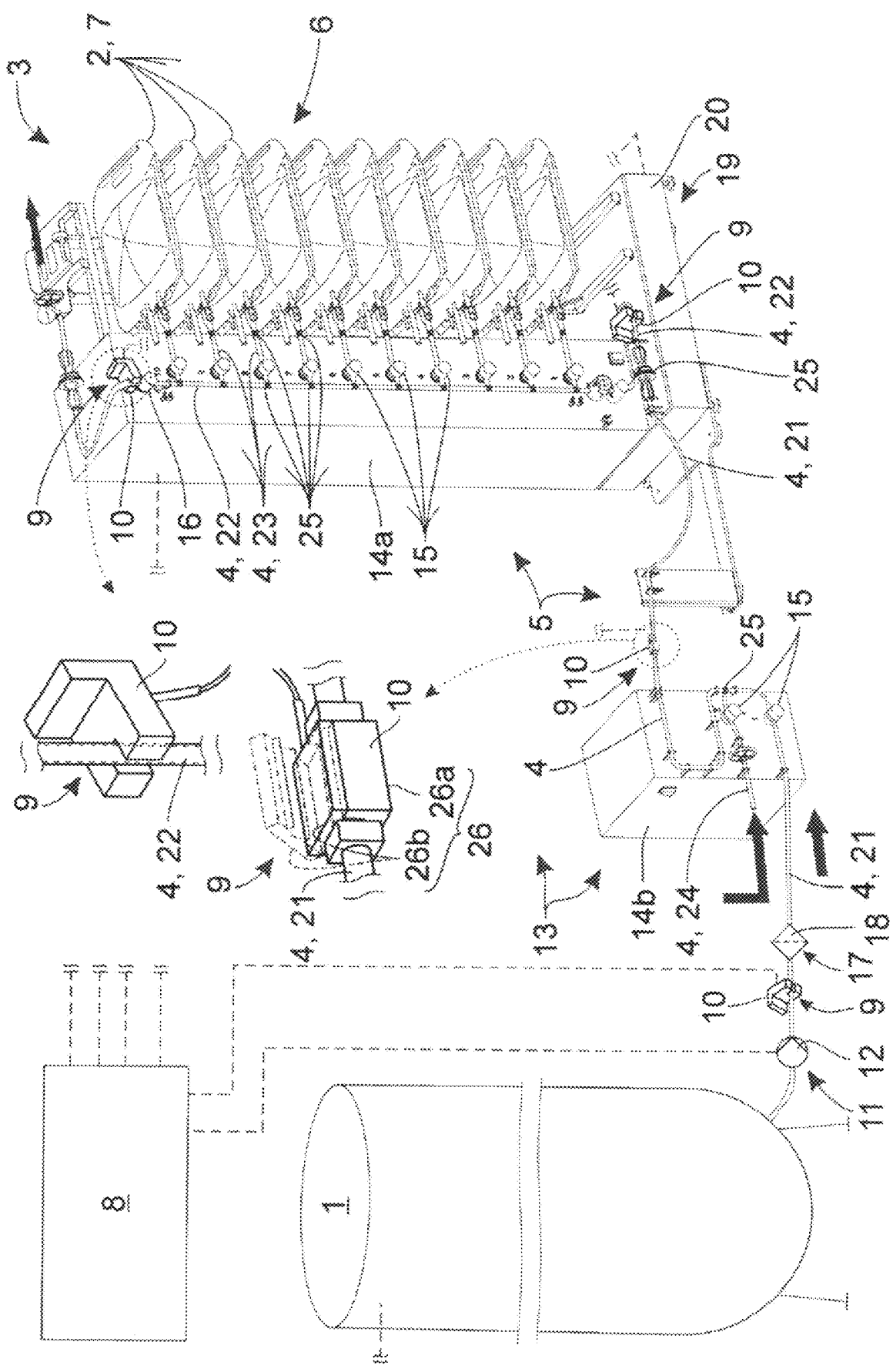

BIOPROCESSING INSTALLATION

CROSS-REFERENCE TO RELATED APPLICATIONS

This application is a national stage application under 35 U.S.C. 371 of International Patent Application Serial No. PCT/EP2020/083698, entitled "Bioprocessing Installation," filed Nov. 27, 2020, which claims priority from European Patent Application No. EP 20 315 021.4, filed Feb. 18, 2020, the disclosure of which is incorporated herein by reference.

FIELD OF THE TECHNOLOGY

Various embodiments relate to a bioprocessing installation, in particular biopharmaceutical installation, a computer-implemented method for controlling such a bioprocessing installation, an electronic control unit for controlling such a bioprocessing installation and a method for operating such a bioprocessing installation.

BACKGROUND

A bioprocessing installation is generally understood to be an apparatus with which biotechnological processes, in particular biopharmaceutical processes, can be carried out or supported. One example for such a biotechnological process is a filling process in which a liquid biological medium, e.g. a biological medical product or substances for the manufacturing of a biological medical product, has to be transferred from a storage container, hereinafter referred to as reservoir tank, to one or more target containers, hereinafter referred to as receiving containers. Another example is the use of a bioreactor to cultivate microorganisms or mammalian cells under given conditions, wherein a fermentation broth is transferred from the bioreactor via a filter arrangement to respective receiving containers. Yet another example is a mixing process in which suspensions, solutions or emulsions that are used in biotechnological processes are mixed and transferred into a fluid line or a receiving container. In all such processes the liquid biological medium is transferred from the respective reservoir tank to the respective receiving container or containers via one or more fluid lines.

The bioprocessing installation (DE 10 2011 000 430 A1) comprises a reservoir tank, a fluid line network with a supply line, fluidically connected to it a main line, from which several branch lines branch off, which each lead to an associated receiving container in the form of a bag. The known bioprocessing installation comprises a fluid valve arrangement with which it is possible to dose the liquid biological medium in the respective receiving container precisely. Such a bioprocessing installation is also known as multi-fill system.

It is important for the process reliability of a multi-fill system, for example, to prevent overfilling of the receiving containers, especially of product or sample bags. A common method for checking the quantity of the liquid biological medium filled into the respective receiving container is to observe the change in weight of the respective receiving container during the filling process. However, if the density of the liquid biological medium does not correspond to the expected value, overfilling may occur. This is the case, for example, if gas bubbles or foam are carried in the media-carrying fluid lines. Gas bubbles and foam can occur due to leaks or the suction of foam or air when the reservoir tank runs empty. Up to now, subjective optical monitoring by the user has been typical. This, however, is often inaccurate and may delay the filling process unnecessarily.

SUMMARY

It is therefore an object of the present disclosure to provide a bioprocessing installation, in particular biopharmaceutical installation, with which monitoring is more accurate and a transfer or filling process more efficient.

The above noted problem is solved for a bioprocessing installation, in particular biopharmaceutical installation, with the features of embodiments described herein.

The idea underlying some embodiments is to have a bioprocessing installation, e.g. a multi-fill system, equipped with one or more gas bubble sensors to evaluate the gas content in the liquid biological medium. Based on the result of such a detection an electronic control unit can intervene automatically and, for example, interrupt, change or influence the transfer of the liquid biological medium. According to an embodiment thereby overfilling can be prevented. For this purpose, the electronic control unit is, among other things, able to influence fluid pumps and/or valves of the bioprocessing installation. Thereby, the process becomes more accurate and more efficient.

In detail, it is proposed that the bioprocessing installation comprises a sensor arrangement with at least one gas bubble sensor, which sensor arrangement is configured to detect one or more gas bubbles, foam or separated phases in the liquid biological medium by means of a gas bubble sensor and to generate one or more corresponding sensor signals, and that the electronic control unit is configured to monitor the transfer of the liquid biological medium from the reservoir tank in the direction of the at least one receiving container based on the one or more sensor signals generated by the sensor arrangement.

Various embodiments relate to additional components which further improve the proposed bioprocessing installation. At least one embodiment defines a fluid pump arrangement with at least one fluid pump to apply kinetic energy to the liquid biological medium. At least one embodiment is directed to a fluid valve arrangement with at least one valve unit, wherein each valve unit contains at least one fluid valve, to control, in particular to close, the flowable cross-section of the respective fluid line. At least one embodiment relates to a filter arrangement with at least one filter to filter the liquid biological medium in the respective fluid line. At least one embodiment defines a weighing arrangement with at least one scale to determine a filling weight of at least one receiving container.

According to various embodiments the fluid lines are part of a fluid line network which comprises, in the fluid flowing direction from the reservoir tank to the receiving container, a supply line and/or a main line fluidically connected to the supply line and, in some embodiments, one or more branch lines branching off from the main line. A supply line is a fluid line starting at the reservoir tank and receiving the liquid biological medium out of the reservoir tank. A main line is a fluid line fluidically connecting the supply line with one or more receiving containers, such as by the branch lines. Each branch line ends in or at an associated receiving container. Moreover, the fluid line network may contain an air supply line, in particular to direct air, e.g. compressed air, into the fluid line network and/or into the respective fluid line, e.g. into the supply line and/or into the main line and/or into the one or more branch lines, to thereby remove any liquid biological medium from the respective fluid line in the course of an emptying process.

According to various embodiments the respective fluid lines are fluidically connected to each other via a respective coupling point. In various embodiments, a gas bubble sensor is positioned directly downstream of the respective coupling point. "Directly" means that there is no further component arranged between the coupling point and the bubble sensor which is fluidically connected to the respective fluid line.

Various embodiments define positions to place a gas bubble sensor in the bioprocessing installation. In particular, at least one gas bubble sensor may be positioned between the reservoir tank and the at least one receiving container. Additionally or alternatively, at least one gas bubble sensor may be positioned downstream of the at least one receiving container or downstream of the unit consisting of one or more receiving containers (downstream of all points where fluid lines branch off to the receiving containers), such as downstream of a venting valve. Additionally or alternatively, at least one gas bubble sensor may be positioned between the reservoir tank and a valve unit, in some embodiments, comprising an air inlet. Additionally or alternatively, at least one gas bubble sensor may be positioned between a valve unit, in some embodiments, comprising an air inlet and a further valve unit in particular comprising one or more fluid valves each associated with a receiving container. Additionally or alternatively, at least one gas bubble sensor may be positioned at a fluid line on a valve unit in particular comprising one or more fluid valves each associated with a receiving container.

Various embodiments provide sensor types of the at least one gas bubble sensor.

According to various embodiments, at a measuring point, the respective gas bubble sensor is connected to the fluid line, that is the sensor is in contact with the fluid line, in particular its outer circumferential surface, without penetrating the fluid line. Alternatively, the respective gas bubble sensor is inserted into the fluid line thereby coming into direct contact with the liquid biological medium, or is spaced from the fluid line. "Spaced" in this regard means, that there is at least a small gap between the outer circumferential surface of the respective fluid line and the gas bubble sensor.

According to various embodiments the detection of gas bubbles or foam is carried out continuously or intermittently.

At least one embodiment defines an electronic control unit which controls the transfer of the liquid biological medium and/or generates when necessary an acoustic and/or optical alarm.

Various embodiments specify particularly use cases for the proposed bioprocessing installation. Optional use cases are in particular a flooding and/or venting process, an emptying process, or an overfill protection process.

Various embodiments are directed to a computer implemented-method for controlling a bioprocessing installation, in particular a bioprocessing installation according to the disclosure. The method comprises monitoring the transfer of the liquid biological medium from the reservoir tank in the direction of the at least one receiving container based on one or more sensor signals received from a sensor arrangement. All explanations given for the bioprocessing installation according to the first teaching are fully applicable to this teaching.

Various embodiments are directed to an electronic control unit comprising one or more processors configured to perform the computer implemented-method according to the disclosure. All explanations given for the bioprocessing installation according to the first teaching and for the computer implemented-method according to the second teaching are also fully applicable to this teaching.

Various embodiments are directed to a method for operating a bioprocessing installation. All explanations given in respect to the bioprocessing installation according to the disclosure, for the computer implemented-method according to the disclosure and for the electronic control unit according to the disclosure are also fully applicable to this teaching.

Various embodiments provide a bioprocessing installation, in particular biopharmaceutical installation, comprising a reservoir tank, one or more fluid lines, one or more receiving containers and an electronic control unit, wherein at least one fluid line fluidically connects the reservoir tank to at least one receiving container, wherein a liquid biological medium can be transferred, in particular pumped, from the reservoir tank through the at least one fluid line into the at least one receiving container, wherein the bioprocessing installation comprises a sensor arrangement with at least one gas bubble sensor, which sensor arrangement is configured to detect one or more gas bubbles, foam and/or separated phases in the liquid biological medium by means of a gas bubble sensor and to generate one or more corresponding sensor signals, and the electronic control unit is configured to monitor the transfer of the liquid biological medium from the reservoir tank in the direction of the at least one receiving container based on the one or more sensor signals generated by the sensor arrangement.

In some embodiments, it comprises a fluid pump arrangement with at least one fluid pump, which fluid pump arrangement is configured to apply kinetic energy to the liquid biological medium in the respective fluid line in the section of the bioprocessing installation between the reservoir tank and the at least one receiving container, in some embodiments, in that the pump arrangement is actuated by the electronic control unit based on the one or more sensor signals generated by the sensor arrangement.

In some embodiments, it comprises a fluid valve arrangement with at least one valve unit each containing at least one fluid valve, in particular a pinch valve, which fluid valve arrangement is configured by means of a fluid valve of the respective valve unit to control, in particular to close, the flowable cross-section of the respective fluid line, in particular in the section of the bioprocessing installation between the reservoir tank and the at least one receiving container and/or in the section of the bioprocessing installation downstream of the at least one receiving container and/or in the section of the bioprocessing installation downstream of the unit consisting of one or more receiving containers, in some embodiments, in that the fluid valve arrangement is actuated by the electronic control unit based on the one or more sensor signals generated by the sensor arrangement.

In some embodiments, it comprises a filter arrangement with at least one filter, which filter arrangement is configured to filter the liquid biological medium in the respective fluid line in the section of the bioprocessing installation between the reservoir tank and the at least one receiving container.

In some embodiments, it comprises a weighing arrangement with at least one scale, which weighing arrangement is configured to determine a filling weight of the at least one receiving container and to generate one or more corresponding sensor signals, in some embodiments, in that the electronic control unit is configured to monitor the transfer of the liquid biological medium from the reservoir tank in the direction of the at least one receiving container based on the one or more sensor signals generated by the weighing arrangement.

In some embodiments, the fluid lines are part of a fluid line network of the bioprocessing installation, which fluid line network comprises, as fluid lines, a supply line between the reservoir tank and a valve unit of the fluid valve arrangement, which valve unit in particular comprises one or more fluid valves each associated with a receiving container, and/or a main line on a valve unit of the fluid valve arrangement, which valve unit in particular comprises one or more fluid valves each associated with a receiving container, in some embodiments, one or more branch lines on a valve unit of the fluid valve arrangement branching off from the main line, which valve unit in particular comprises one or more fluid valves each associated with a receiving container, and/or an air supply line on a valve unit of the fluid valve arrangement, which valve unit comprises one or more fluid valves and which valve unit is arranged in particular between the reservoir tank and a further valve unit, which further valve unit in particular comprises one or more fluid valves each associated with a receiving container.

In some embodiments, via a respective coupling point, the supply line is fluidically coupled to the main line and/or the main line is fluidically coupled to the respective branch line and/or the respective branch line is fluidically coupled to the respective receiving container and/or the air supply line is fluidically coupled to the supply line, in some embodiments, in that a gas bubble sensor of the sensor arrangement is positioned directly downstream of the respective coupling point.

In some embodiments, at least one gas bubble sensor of the sensor arrangement is positioned in the section of the bioprocessing installation through which the liquid biological medium flows, between the reservoir tank and the at least one receiving container, at a fluid line, in particular supply line, main line, branch line or air supply line.

In some embodiments, at least one gas bubble sensor of the sensor arrangement is positioned in the section of the bioprocessing installation through which the liquid biological medium flows, downstream of the at least one receiving container or the unit consisting of one or more receiving containers, in some embodiments, downstream of a venting valve of a valve unit of the fluid valve arrangement, at a fluid line, in particular main line.

In some embodiments, at least one gas bubble sensor of the sensor arrangement is positioned in the section of the bioprocessing installation through which the liquid biological medium flows, between the reservoir tank and a valve unit of the fluid valve arrangement, in particular valve unit comprising an air inlet, at a fluid line.

In some embodiments, at least one gas bubble sensor of the sensor arrangement is positioned at a fluid line in the section of the bioprocessing installation through which the liquid biological medium flows, between a valve unit of the fluid valve arrangement, in particular valve unit comprising an air inlet, and a further valve unit of the fluid valve arrangement, which further valve unit in particular comprises one or more fluid valves each associated with a receiving container.

In some embodiments, at least one gas bubble sensor of the sensor arrangement is positioned at a fluid line in the section of the bioprocessing installation through which the liquid biological medium flows, on a valve unit which in particular comprises one or more fluid valves each associated with a receiving container, in some embodiments, in that a gas bubble sensor is positioned upstream of the at least one coupling point of the main line with the respective branch line and/or a gas bubble sensor is positioned downstream of the at least one coupling point of the main line with the respective branch line.

In some embodiments, at least one gas bubble sensor of the sensor arrangement is an ultrasonic sensor, an optical sensor, a conductive sensor, an inductive sensor or a capacitive sensor.

In some embodiments, at a measuring point, the respective gas bubble sensor is connected to the fluid line, in particular via a clamping connection, or is inserted into the fluid line or is spaced from the fluid line.

In some embodiments, the sensor arrangement and/or the respective gas bubble sensor carries out a continuous or intermittent detection.

In some embodiments, the electronic control unit is configured, based on the one or more sensor signals generated by the sensor arrangement and in particular based on the one or more sensor signals generated by the weighing arrangement, to control the transfer of the liquid biological medium from the reservoir tank in the direction of the at least one receiving container and/or to generate an acoustic and/or optical alarm.

In some embodiments, one or more sensor signals generated by the sensor arrangement contain information about the gas and/or foam concentration in the liquid biological medium and/or information as to whether the gas or foam concentration in the liquid biological medium has exceeded or fallen below a limit value.

In some embodiments, the electronic control unit is configured, based on the one or more sensor signals generated by the sensor arrangement and in particular based on the one or more sensor signals generated by the weighing arrangement, to monitor the transfer of the liquid biological medium from the reservoir tank in the direction of the at least one receiving container in the course of a flooding and/or venting process of one or more fluid lines and/or in the course of an emptying process of one or more fluid lines and/or in the course of a monitoring of the gas and/or foam concentration in the liquid biological medium during the transfer of the liquid biological medium into the at least one receiving container and/or in the course of an overfill protection process.

Various embodiments provide a computer-implemented method for controlling a bioprocessing installation, in particular biopharmaceutical installation, in some embodiments, a bioprocessing installation according to the disclosure, the bioprocessing installation comprising a reservoir tank, one or more fluid lines, one or more receiving containers, wherein at least one fluid line fluidically connects the reservoir tank to at least one receiving container, wherein a liquid biological medium can be transferred, in particular pumped, from the reservoir tank through the at least one fluid line into the at least one receiving container, the method comprising: monitoring, by means of an electronic control unit, the transfer of the liquid biological medium from the reservoir tank in the direction of the at least one receiving container based on one or more sensor signals received from a sensor arrangement of the bioprocessing installation, which sensor arrangement is configured to detect one or more gas bubbles, foam and/or separated phases in the liquid biological medium by means of at least one gas bubble sensor and to generate the one or more corresponding sensor signals.

Various embodiments provide an electronic control unit for controlling a bioprocessing installation, the electronic control unit comprising one or more processors configured to perform the method described herein.

Various embodiments provide a method for operating a bioprocessing installation, in particular biopharmaceutical installation, such as a bioprocessing installation as described herein, the bioprocessing installation comprising a reservoir tank, one or more fluid lines, one or more receiving containers and an electronic control unit, wherein at least one fluid line fluidically connects the reservoir tank to at least one receiving container, wherein a liquid biological medium is transferred, in particular pumped, from the reservoir tank through the at least one fluid line into the at least one receiving container, wherein one or more gas bubbles, foam and/or separated phases in the liquid biological medium are detected by means of at least one gas bubble sensor of a sensor arrangement of the bioprocessing installation and one or more corresponding sensor signals are generated by means of the sensor arrangement, and wherein the transfer of the liquid biological medium from the reservoir tank in the direction of the at least one receiving container is monitored by means of the electronic control unit based on the one or more sensor signals generated by the sensor arrangement.

BRIEF DESCRIPTION OF THE DRAWINGS

In the following, an embodiment of the disclosure is explained with respect to the drawing. In the drawing FIGURE shows a schematic view of one embodiment of the proposed bioprocessing installation.

DETAILED DESCRIPTION

The shown bioprocessing installation, in particular biopharmaceutical installation, is used to transfer a liquid biological medium from a reservoir tank 1 to one or more receiving containers 2. A liquid biological medium may be in the form of a single-phase liquid, but may also be a multi-phase system comprising a liquid phase.

In the present exemplary embodiment several receiving containers 2 are provided as part of a so called "manifold". A manifold 3 is a unit comprising flexible bags as receiving containers 2, as well as several fluid lines 4, in particular hoses. Here, the fluid lines 4 are part of a fluid line network 5, which will be described later more precisely. Here the manifold 3 comprising the bag-type receiving containers 2 and at least some of the fluid lines 4, in particular all fluid lines 4, of the fluid line network 5, are provided as a preassembled and/or preconfigured unit. In some embodiments, this unit is a single-use unit and/or the receiving containers 2 and/or fluid lines 4 are single-use components.

Such a bioprocessing installation comprising a reservoir tank 1 and several receiving containers 2, in particular as part of a manifold 3, is also known as multi-fill system.

In the shown embodiment the manifold 3 is installed by placing the receiving containers 2, here the bags, in a storage rack 6 and fixing the fluid lines 4, here the hoses, at different points, in particular on corresponding holders 7, of the bioprocessing installation. Here, for example, ten receiving containers 2 are placed in the storage rack 6. Here, the storage rack 6 is used to accommodate the receiving containers 2, here the bags, in a horizontal orientation. According to an alternative embodiment (not shown) the storage rack 6 may be provided in the form of a hanging frame to accommodate hanging bags in a vertical orientation.

Moreover, the bioprocessing installation comprises an electronic control unit 8 which is electronically coupled to several of the components of the bioprocessing installation, what is shown by dashed lines in the FIGURE.

In the proposed bioprocessing installation at least one fluid line 4 fluidically connects the reservoir tank 1 to the at least one receiving container 2, wherein the liquid biological medium can be transferred, in particular pumped, from the reservoir tank 1 through the at least one fluid line 4 into the at least one receiving container 2.

In various embodiments, the bioprocessing installation comprises a sensor arrangement 9 with at least one gas bubble sensor 10, which sensor arrangement 9 is configured to detect one or more gas bubbles, foam and/or separated phases in the liquid biological medium by means of a gas bubble sensor 10 and to generate one or more corresponding sensor signals, and, on the other hand, the electronic control unit 8 is configured to monitor the transfer of the liquid biological medium from the reservoir tank 1 in the direction of the at least one receiving container 2 based on the one or more sensor signals generated by the sensor arrangement 9.

Gas bubble sensors, also known as bubble sensors, are sensors configured to detect the presence of one single gas bubble, a plurality of gas bubbles, foam and/or separated phases in a liquid medium flowing through a fluid line.

When the liquid biological medium flows through the fluid line network 5 or the respective fluid line 4, by means of the sensor arrangement 9, which here for example comprises four gas bubble sensors 10 at different positions, one or more sensor signals can be generated, which one or more sensor signals contain information about the gas and/or foam concentration in the liquid biological medium. Additionally or alternatively the one or more sensor signals may contain information as to whether the gas or foam concentration in the liquid biological medium has exceeded or fallen below a limit value. Such a limit value is in particular predetermined in the electronic control unit 8 and may for example be entered by the user.

Here the electronic control unit 8 is configured to monitor the transfer of the liquid biological medium from the reservoir tank 1 in the direction (direction of flow) of the at least one receiving container 2 in the course of a flooding and/or venting process of one or more fluid lines 4. Additionally or alternatively, the electronic control unit 8 can be configured to monitor the transfer of the liquid biological medium from the reservoir tank 1 in the direction of the at least one receiving container 2 in the course of an emptying process of one or more fluid lines 4. Additionally or alternatively the electronic control unit 8 can be configured to monitor the transfer of the liquid biological medium from the reservoir tank 1 to the at least one receiving container 2 in the course of a monitoring of the gas and/or foam concentration in the liquid biological medium during the transfer of the liquid biological medium into the at least one receiving container 2. Additionally or alternatively, the electronic control unit 8 can be configured to monitor the transfer of the liquid biological medium from the reservoir tank 1 in the direction of the at least one receiving container 2 in the course of an overfill protection process, that is a process to prevent the receiving containers from becoming too full or from overflowing.

For the uses described above, the proposed bioprocessing installation has the following exemplary structure and/or comprises one or more of the following components.

Here the proposed bioprocessing installation comprises a fluid pump arrangement 11 with at least one fluid pump 12, here for example one single fluid pump 12. Alternatively, two or more fluid pumps 12 may be provided. The fluid pump arrangement 11 is configured to apply kinetic energy to the liquid biological medium in the respective fluid line 4 in the section of the bioprocessing installation between the reservoir tank 1 and the at least one receiving container 2. In some embodiments, the pump arrangement 11 is actuated by the electronic control unit 8 based on the one or more sensor signals generated by the sensor arrangement 9.

Here the fluid pump 12 is positioned, as an example, directly downstream of the reservoir tank 1.

Furthermore, the bioprocessing installation of the present exemplary embodiment here comprises a fluid valve arrangement 13 with at least one valve unit 14a, 14b. Here, two valve units 14a, 14b are provided.

Each valve unit 14a, 14b contains at least one fluid valve 15, in particular a pinch valve. The fluid valve arrangement 13 is configured by means of a fluid valve 15 of the respective valve unit 14a, 14b to control, in particular to close, the flowable cross-section of the respective fluid line 4. In particular, the fluid valve arrangement 13 is configured to control, in particular to close, the flowable cross-section of the respective fluid line 4 in the section of the bioprocessing installation between the reservoir tank and the at least one receiving container 2. Additionally or alternatively, as shown in the FIGURE, the fluid valve arrangement 13 may be configured to control, in particular to close, the flowable cross-section of the respective fluid line 4 in the section of the bioprocessing installation downstream of the at least one receiving container 2 and/or in the section of the bioprocessing installation downstream of the unit consisting of one or more receiving containers 2 (downstream of all points where fluid lines branch off to the receiving containers 2). The section downstream of the at least one receiving container 2, in at least some embodiments, comprises a venting valve 16 as one of the fluid valves 15. Here the fluid valve arrangement 13 is actuated by the electronic control unit 8 based on the one or more sensor signals generated by the sensor arrangement 9.

Moreover, as can also be seen in the FIGURE, the proposed bioprocessing installation may comprise a filter arrangement 17 with at least one filter 18. The filter arrangement 17 may be configured to filter the liquid biological medium in the respective fluid line 4 in the section of the bioprocessing installation between the reservoir tank 1 and the at least one receiving container 2. A filter 18 is for example positioned where two fluid lines 4 are fluidically coupled to each other and/or directly downstream of an inlet and/or directly upstream of an outlet.

Here, the proposed bioprocessing installation also comprises a weighing arrangement 19 with at least one scale 20. The weighing arrangement 19 may be configured to determine a filling weight of the at least one receiving container 2 and to generate one or more corresponding sensor signals. Here, one single scale 20 is provided, which scale 20 is arranged below the storage rack 6, such that the total filling weight of all receiving containers 2 may be determined. By filling one receiving container 2 after the other, also the individual filling weight of each receiving container 2 may be determined. Here, the electronic control unit 8 is configured to monitor the transfer of the liquid biological medium from the reservoir tank 1 in the direction of the at least one receiving container 2 also based on one or more sensor signals generated by the weighing arrangement 19. In particular, the electronic control unit 8 is configured to monitor the transfer of the liquid biological medium not only based on the one or more sensor signals generated by the sensor arrangement 9, but also on the one or more sensor signals generated by the weighing arrangement 19.

Now an embodiment of the fluid line network 5 of the bioprocessing installation is described in further detail.

Here the fluid line network 5 comprises, as fluid lines 4, a supply line 21 and/or a main line 22, in some embodiments, also one or more branch lines 23 branching off from the main line 22, and/or an air supply line 24.

Here, the supply line 21 is installed between the reservoir tank 1 and a valve unit 14a of the fluid valve arrangement 13, which valve unit 14a in particular comprises one or more fluid valves 15 each associated with a receiving container 2.

Here, the main line 22 is installed on a vale unit 14a of the fluid valve arrangement 13, here on the same valve unit 14a as mentioned before, which valve unit 14a in particular comprises one or more fluid valves 15 each associated with a receiving container 2. The main line 22 is here coupled, downstream of the supply line 21, to the supply line 21.

Here the branch lines 23 are installed on a valve unit 14a of the fluid valve arrangement 13, here also on the same valve unit 14a as mentioned before, which valve unit 14a in particular comprises one or more fluid valves 15 each associated with a receiving container 2. The branch lines 23 all branch off from the main line 22 and fluidically connect the main line 22 with the receiving containers 2.

Here, the air supply line 24 is installed on a valve unit 14b of the fluid valve arrangement 13, which valve unit 14b comprises one or more fluid valves 15 and which valve unit 14b is different from above valve unit 14a. This valve unit 14b is arranged in particular between the reservoir tank 1 and a further valve unit 14a, here the above mentioned valve unit 14a, which further valve unit 14a in particular comprises one or more fluid valves 15 each associated with a receiving container 2. The air supply line 24 here drains into the supply line 21.

One or more of the described fluid lines 4, 21, 22, 23, 24 can be formed as a hose or alternatively as a piping. A hose is here a flexible fluid line 4 whereas a piping is a rigid tube as fluid line 4. In some embodiments, one or more of the fluid lines 4 are transparent at least in sections, which may be necessary for some specific type of gas bubble sensor 10, in particular an optical gas bubble sensor 10.

Moreover, as shown in the FIGURE of the exemplary embodiment, several coupling points 25 are provided where one of the fluid lines 4 is coupled to another one of the fluid lines 4. Here, via such a coupling point 25 the supply line 21 is fluidically coupled to the main line 22 and/or the main line 22 is fluidically coupled to the respective branch line 23 and/or the respective branch line 23 is fluidically coupled to the respective receiving container 2 and/or the air supply line 24 is fluidically coupled to the supply line 21.

Here, upstream of the coupling point 25 where the air supply line 24 is coupled to the supply line 21, a fluid valve 15 is installed in the supply line 21. Moreover, upstream of this coupling point 25 where the air supply line 24 is coupled to the supply line 21, a further fluid valve 15 is installed in the air supply line 24. Moreover, upstream of the first coupling point 25 where a branch line 23 is coupled to the main line 23, a further fluid valve 15 is installed in the main line 22. Moreover, downstream of the last coupling point 25 where a branch line 23 is coupled to the main line 23, a further fluid valve 15 is installed in the main line 22. Moreover, downstream of each coupling point 25 where the respective branch line 23 is fluidically connected to the main line 22, a respective fluid valve 15 is installed in the respective branch line 23.

Here, a gas bubble sensor 10 of the sensor arrangement 9 is positioned directly downstream of one or more, in particular each, of the named coupling points 25. Various positions for such a gas bubble sensor 10 are shown in the FIGURE and described in the following.

In particular it can be that at least one gas bubble sensor 10 of the sensor arrangement 9 is positioned in the section of the bioprocessing installation through which the liquid biological medium flows, between the reservoir tank 1 and the at least one receiving container 2, at a fluid line 4, in particular supply line 21, main line 22, branch line 23 or air supply line 24.

Moreover, it is conceivable that at least one gas bubble sensor 10 of the sensor arrangement 9 is positioned in the section of the bioprocessing installation through which the liquid biological medium flows, downstream of the at least one receiving container 2 or, as shown in the FIGURE, downstream of the unit consisting of one or more receiving containers 2 (downstream of all points where fluid lines 23 branch off to the receiving containers 2), here the ten receiving containers 2, in some embodiments, downstream of a venting valve 16 of a valve unit 14a of the fluid valve arrangement 13, at a fluid line 4, in particular main line 22.

Furthermore, at least one gas bubble sensor 10 of the sensor arrangement 9 may be positioned in the section of the bioprocessing installation through which the liquid biological medium flows, between the reservoir tank 1 and a valve unit 14a, 14b of the fluid valve arrangement 13, in particular valve unit 14b comprising an air inlet, at a fluid line 4.

It is conceivable that at least one gas bubble sensor 10 of the sensor arrangement 9 is positioned at a fluid line 4 in the section of the bioprocessing installation through which the liquid biological medium flows, between a valve unit 14b of the fluid valve arrangement 13, in particular valve unit 14b comprising an air inlet, and a further valve unit 14a of the fluid valve arrangement 13, which further valve unit 14a in particular comprises one or more fluid valves 15 each associated with a receiving container 2.

Moreover, in some embodiments, at least one gas bubble sensor 10 of the sensor arrangement 9 is positioned at a fluid line 4 in the section of the bioprocessing installation through which the liquid biological medium flows, on a valve unit 14a which in particular comprises one or more fluid valves 15 each associated with a receiving container 2, in some embodiments, in that a gas bubble sensor 10 is positioned upstream of the at least one coupling point 25 of the main line 22 with the respective branch line 23 and/or a gas bubble sensor 10 is positioned downstream of the at least one coupling point 25 of the main line 22 with the respective branch line.

One or more of the gas bubble sensors 10 of the sensor arrangement 9 may be in the form of an ultrasonic sensor, an optical sensor, a conductive sensor, an inductive senor or a capacitive sensor.

At a corresponding measuring point, the respective gas bubble sensor 10 can be connected to the fluid line 4, in particular by attaching it laterally, whereby a clamp or snap-in connection can be established between gas bubble sensor 10 and fluid line 4. The connection can also be secured to prevent the gas bubble sensor 10 from slipping or falling off. It is also conceivable to use a sensor housing 26 with two housing parts 26a, 26b that can be pivoted and folded towards each other, which housing parts 26a, 26b in the unfolded state are placed around the fluid line 4 from both sides and then folded together. Alternatively the respective gas bubble sensor 10 can be inserted into the fluid line 4 or can be spaced from the fluid line 4.

Here the sensor arrangement 9 and/or the respective gas bubble sensor 10 carries out a continuous or intermittent detection.

According to various embodiments, a computer implemented-method for controlling a bioprocessing installation is provided. The method comprises: monitoring, by means of an electronic control unit 8, the transfer of the liquid biological medium from the reservoir tank 1 in the direction of the at least one receiving container 2 based on one or more sensor signals received from a sensor arrangement 9 of the bioprocessing installation, which sensor arrangement 9 is configured to detect one or more gas bubbles, foam and/or separated phases in the liquid biological medium by means of at least one gas bubble sensor 10 and to generate the one or more corresponding sensor signals. Reference is made to the explanations given above in respect to the bioprocessing installation according to the disclosure and in particular to the operation of the electronic control unit 8.

According to various embodiments, an electronic control unit 8 for controlling a bioprocessing installation is provided, the electronic control unit 8 comprising one or more processors configured to perform the method according to the second teaching. The electronic control unit 8 may comprise a non-volatile memory storing specific executable instructions, the instructions being configured to implement the computer implemented-method according to the second teaching when executed on the one or more processors. Reference is made to the explanations given for the first and second teaching.

According to various embodiments, a method for operating a bioprocessing installation is provided. A liquid biological medium is transferred, in particular pumped, such as by the fluid pump arrangement 11, from the reservoir tank 1 through the at least one fluid line 4 into the at least one receiving container 2. One or more gas bubbles, foam and/or separated phases in the liquid biological medium are detected by means of at least one gas bubble sensor 10 of a sensor arrangement 9 of the bioprocessing installation and one or more corresponding sensor signals are generated by means of the sensor arrangement 9. The transfer of the liquid biological medium from the reservoir tank 1 in the direction of the at least one receiving container 2 is monitored by means of the electronic control unit 8 based on the one or more sensor signals generated by the sensor arrangement 9. Reference is made to the explanations given for the first, second, and third teaching and in particular to the operation of the components of the bioprocessing installation according to the disclosure.

The invention claimed is:

1. A bioprocessing installation set up as a multi-fill system, comprising:
   a reservoir tank,
   one or more fluid lines,
   one or more receiving containers, and
   an electronic control unit,
   wherein at least one fluid line fluidically connects the reservoir tank to at least one receiving container,
   wherein a liquid biological medium can be transferred from the reservoir tank through the at least one fluid line into the at least one receiving container,
   wherein the bioprocessing installation comprises a sensor arrangement with at least one gas bubble sensor, which sensor arrangement is configured to detect one or more gas bubbles, foam and/or separated phases in the liquid biological medium by a gas bubble sensor and to generate one or more corresponding sensor signals, and
   wherein the electronic control unit is configured to monitor the transfer of the liquid biological medium from the reservoir tank in the direction of the at least one receiving container in the course of an overfill protection process based on the one or more sensor signals generated by the sensor arrangement.

2. The bioprocessing installation according to claim 1, further comprises a fluid pump arrangement with at least one fluid pump, which fluid pump arrangement is configured to apply kinetic energy to the liquid biological medium in the respective fluid line in the section of the bioprocessing installation between the reservoir tank and the at least one receiving container.

3. The bioprocessing installation according to claim 1, further comprises a fluid valve arrangement with at least one valve unit each containing at least one fluid valve, which fluid valve arrangement is configured by a fluid valve of the respective valve unit to control the flowable cross-section of the respective fluid line.

4. The bioprocessing installation according to claim 1, further comprises a filter arrangement with at least one filter, which filter arrangement is configured to filter the liquid biological medium in the respective fluid line in the section of the bioprocessing installation between the reservoir tank and the at least one receiving container.

5. The bioprocessing installation according to claim 1, further comprises a weighing arrangement with at least one scale, which weighing arrangement is configured to determine a filling weight of the at least one receiving container and to generate one or more corresponding sensor signals.

6. The bioprocessing installation according to claim 1, wherein the fluid lines are part of a fluid line network of the bioprocessing installation, which fluid line network comprises, as fluid lines, a supply line between the reservoir tank and a valve unit of the fluid valve arrangement, which valve unit in particular comprises one or more fluid valves each associated with a receiving container, and/or a main line on a valve unit of the fluid valve arrangement.

7. The bioprocessing installation according to claim 6, wherein, via a respective coupling point, the supply line is fluidically coupled to the main line and/or the main line is fluidically coupled to the respective branch line and/or the respective branch line is fluidically coupled to the respective receiving container and/or an air supply line is fluidically coupled to the supply line, preferably in that a gas bubble sensor of the sensor arrangement is positioned directly downstream of the respective coupling point.

8. The bioprocessing installation according to claim 1, wherein at least one gas bubble sensor of the sensor arrangement is positioned in the section of the bioprocessing installation through which the liquid biological medium flows, between the reservoir tank and the at least one receiving container, at a fluid line.

9. The bioprocessing installation according to claim 1, wherein at least one gas bubble sensor of the sensor arrangement is positioned in the section of the bioprocessing installation through which the liquid biological medium flows, downstream of the at least one receiving container or the unit consisting of one or more receiving containers.

10. The bioprocessing installation according to claim 1, wherein at least one gas bubble sensor of the sensor arrangement is positioned in the section of the bioprocessing installation through which the liquid biological medium flows, between the reservoir tank and a valve unit of the fluid valve arrangement at a fluid line.

11. The bioprocessing installation according to claim 1, wherein at least one gas bubble sensor of the sensor arrangement is positioned at a fluid line in the section of the bioprocessing installation through which the liquid biological medium flows, between a valve unit of the fluid valve arrangement and a further valve unit.

12. The bioprocessing installation according to claim 1, wherein at least one gas bubble sensor of the sensor arrangement is positioned at a fluid line in the section of the bioprocessing installation through which the liquid biological medium flows, on a valve unit.

13. The bioprocessing installation according to claim 1, wherein at least one gas bubble sensor of the sensor arrangement is an ultrasonic sensor, an optical sensor, a conductive sensor, an inductive sensor or a capacitive sensor.

14. The bioprocessing installation according to claim 1, wherein, at a measuring point, the respective gas bubble sensor is connected to the fluid line, or is inserted into the fluid line or is spaced from the fluid line.

15. The bioprocessing installation according to claim 1, wherein the sensor arrangement and/or the respective gas bubble sensor carries out a continuous or intermittent detection.

16. The bioprocessing installation according to claim 1, wherein the electronic control unit is configured, based on the one or more sensor signals generated by the sensor arrangement, to control the transfer of the liquid biological medium from the reservoir tank in the direction of the at least one receiving container and/or to generate an acoustic and/or optical alarm.

17. The bioprocessing installation according to claim 1, wherein one or more sensor signals generated by the sensor arrangement contain information about the gas and/or foam concentration in the liquid biological medium and/or information as to whether the gas or foam concentration in the liquid biological medium has exceeded or fallen below a limit value.

18. The bioprocessing installation according to claim 1, wherein the electronic control unit is configured, based on the one or more sensor signals generated by the sensor arrangement, to monitor the transfer of the liquid biological medium from the reservoir tank in the direction of the at least one receiving container in the course of a flooding and/or venting process of one or more fluid lines and/or in the course of an emptying process of one or more fluid lines and/or in the course of a monitoring of the gas and/or foam concentration in the liquid biological medium during the transfer of the liquid biological medium into the at least one receiving container and/or in the course of an overfill protection process.

19. A computer-implemented method for controlling a multi-fill bioprocessing installation, the bioprocessing installation comprising a reservoir tank, one or more fluid lines, one or more receiving containers, wherein at least one fluid line fluidically connects the reservoir tank to at least one receiving container, wherein a liquid biological medium can be transferred from the reservoir tank through the at least one fluid line into the at least one receiving container, the method comprising:

monitoring, by an electronic control unit, the transfer of the liquid biological medium from the reservoir tank in the direction of the at least one receiving container in an overfill protection process based on one or more sensor signals received from a sensor arrangement of the bioprocessing installation, which sensor arrangement is configured to detect one or more gas bubbles, foam and/or separated phases in the liquid biological medium by at least one gas bubble sensor and to generate the one or more corresponding sensor signals.

20. An electronic control unit for controlling a bioprocessing installation, the electronic control unit comprising one or more processors configured to perform the method according to claim 19.

21. A method for operating a multi-fill bioprocessing installation, the bioprocessing installation comprising a reservoir tank, one or more fluid lines, one or more receiving containers and an electronic control unit, wherein at least one fluid line fluidically connects the reservoir tank to at least one receiving container, wherein a liquid biological medium is transferred from the reservoir tank through the at least one fluid line into the at least one receiving container, wherein one or more gas bubbles, foam and/or separated phases in the liquid biological medium are detected by at least one gas bubble sensor of a sensor arrangement of the bioprocessing installation and one or more corresponding sensor signals are generated by the sensor arrangement, and wherein the transfer of the liquid biological medium from the reservoir tank in the direction of the at least one receiving container in an overfill protection process is monitored by the electronic control unit based on the one or more sensor signals generated by the sensor arrangement.

* * * * *